(12) United States Patent
Patel et al.

(10) Patent No.: US 7,455,738 B2
(45) Date of Patent: Nov. 25, 2008

(54) LONG FATIGUE LIFE NITINOL

(75) Inventors: Anuja Patel, Sunnyvale, CA (US); Jianhau Yang, Saratoga, CA (US)

(73) Assignee: Paracor Medical, Inc., Sunnyvale, CA (US)

( * ) Notice: Subject to any disclaimer, the term of this patent is extended or adjusted under 35 U.S.C. 154(b) by 759 days.

(21) Appl. No.: 10/694,646

(22) Filed: Oct. 27, 2003

(65) Prior Publication Data

US 2005/0090844 A1  Apr. 28, 2005

(51) Int. Cl.
C22C 19/03 (2006.01)
(52) U.S. Cl. ........................ 148/402; 148/426
(58) Field of Classification Search ............... 148/402, 148/426
See application file for complete search history.

(56) References Cited

U.S. PATENT DOCUMENTS

| | | | |
|---|---|---|---|
| 3,174,851 A | 3/1965 | Buehler et al. | |
| 4,283,233 A | 8/1981 | Goldstein et al. | |
| 4,310,354 A | 1/1982 | Fountain et al. | |
| 4,654,092 A | 3/1987 | Melton | |
| 4,665,906 A | 5/1987 | Jervis | |
| 4,881,981 A | 11/1989 | Thoma et al. | |
| 5,067,957 A | 11/1991 | Jervis | |
| 5,190,546 A | 3/1993 | Jervis | |
| 5,230,348 A * | 7/1993 | Ishibe et al. | 600/585 |
| 5,334,294 A * | 8/1994 | Iwai et al. | 205/684 |
| 5,341,818 A | 8/1994 | Abrams et al. | |
| 5,350,419 A | 9/1994 | Bendel et al. | |
| 5,486,183 A | 1/1996 | Middleman et al. | |
| 5,509,923 A | 4/1996 | Middleman et al. | |
| 5,597,378 A | 1/1997 | Jervis | |
| 5,632,746 A | 5/1997 | Middleman et al. | |
| 5,720,754 A | 2/1998 | Middleman et al. | |
| 5,749,879 A | 5/1998 | Middleman et al. | |
| 5,820,628 A | 10/1998 | Middleman et al. | |
| 5,843,244 A | 12/1998 | Pelton | |
| 5,904,690 A | 5/1999 | Middleman et al. | |
| 6,004,330 A | 12/1999 | Middleman et al. | |
| 6,059,810 A | 5/2000 | Brown et al. | |
| 6,086,610 A | 7/2000 | Duerig et al. | |
| 6,106,642 A | 8/2000 | DiCarlo | |
| 6,179,859 B1 | 1/2001 | Bates et al. | |
| 6,306,141 B1 | 10/2001 | Jervis | |
| 6,375,826 B1 * | 4/2002 | Wang et al. | 205/684 |

(Continued)

FOREIGN PATENT DOCUMENTS

JP  59170247  9/1984

(Continued)

OTHER PUBLICATIONS

S. Russell, *Nitinol Melting and Fabrication*, pp. 1-9, Proceedings of the International Conference on SMST 2000.

(Continued)

*Primary Examiner*—George Wyszomierski
(74) *Attorney, Agent, or Firm*—Fulwider Patton LLP

(57) ABSTRACT

A high fatigue life superelastic nickel-titanium (nitinol) wire, ribbon, sheet, tubing, or the like is disclosed. The nitinol has a 54.5 to 57.0 weight percent nickel with a balance of titanium composition and has less than 30 percent cold work as a final step after a full anneal and before shape setting heat treatment. Through a rotational beam fatigue test, fatigue life improvement of 37 percent has been observed.

16 Claims, 3 Drawing Sheets

Effect of UTS (as received) on Mean Cycles to Failure (heat treated)

$R^2 = 0.8817$

U.S. PATENT DOCUMENTS

| | | | |
|---|---|---|---|
| 6,419,694 | B1 | 7/2002 | Sandock |
| 6,447,523 | B1 | 9/2002 | Middleman et al. |
| 6,533,805 | B1 | 3/2003 | Jervis |
| 6,595,912 | B2 | 7/2003 | Lau et al. |
| 2002/0005047 | A1* | 1/2002 | Beard ............................ 63/3 |
| 2003/0120181 | A1 | 6/2003 | Toma et al. |
| 2004/0216814 | A1 | 11/2004 | Dooley et al. |

OTHER PUBLICATIONS

W. Harrison et al., *The Study of Nitinol Bending Fatigue*, pp. 391-396, Proceedings of the International Conference on SMST 2000.

M. Reinoehl et al., *The Influence of Melt Practice on Final Fatigue Properties of Superelastic NiTi Wires*, pp. 397-403, pp. 1-9, Proceedings of the International Conference on SMST 2000.

C. Kugler et al., *Non-Zero Mean Fatigue Test Protocol for NiTi*, pp. 409-417, Proceedings of the International Conference on SMST 2000.

D. Tolomeo et al., *Cyclic Properties of Superelastic Nitinol: Design Implications*, pp. 471-476, Proceedings of the International Conference on SMST 2000.

A. Pelton et al., *Optimisation of Processing and Properties of Medical Grade Nitinol Wire*, pp. 107-118, MITAT, Jun. 2000.

Z.C. Lin and John Boylan: "The Effect of Cold Work Texture on the Superelastic Characteristics of Nitinol Sheet" Materials Science Forum, vol. 394-395, 2002, pp. 313-316, XP009041321, Switzerland, See experimental section and the first conclusion.

Patent Abstract of Japan, vol. 0090, No. 21 (C-263), Jan. 29, 1985 & JP 59 170247 A (Furukawa Denki Kogyo KK; others: 01), Sep. 26, 1984 abstract.

W. J. Harrison and Z.C. Lin: "the study of nitinol in bending fatigue" SMST-2000 Proceedings of the International Conference on Shape Memory and Superelastic Technologies, 2000, pp. 391-396, EXP009041320, USA, the whole document.

* cited by examiner

LONG FATIGUE LIFE NITINOL

BACKGROUND OF THE INVENTION

The present invention relates to a method and apparatus for providing a superelastic metal alloy having improved fatigue life. In particular, the present invention relates to a long fatigue life nickel-titanium alloy wire, ribbon, tubing, or sheet.

There has been great interest in shape memory and superelastic alloys such as nickel-titanium. This family of alloys, also known as nitinol (i.e., Nickel-Titanium Naval Ordinance Laboratory) is typically made from a nearly equal composition of nickel and titanium. Key to exploiting the performance of nitinol alloys is the phase transformation in the crystalline structure that transitions between an austenitic phase and a martensitic phase. The austenitic phase is commonly referred to as the high temperature phase, and the martensitic phase is commonly referred to as the low temperature phase. The back and forth phase changes is the mechanism for achieving superelasticity and the shape memory effect.

As the name implies, shape memory means that the alloy can be twisted into a particular shape in the martensitic phase, and when heated to the austenitic phase, the metal returns to its remembered shape. In contrast, superelasticity refers to the ultra high elastic behavior of the alloy under stress. Typical reversible strains of up to 8 percent elongation can be achieved in a superelastic nitinol wire as compared to 0.5 percent reversible strain in a steel wire, for example. This superelasticity appears in the austenitic phase when stress is applied to the alloy and the alloy changes from the austenitic phase to the martensitic phase. This particular martensitic phase is more precisely described as stress-induced martensite (SIM), which is unstable at temperatures above $A_f$ (the austenitic finish) temperature. As such, if the applied stress is removed, the stress-induced martensite reverts back to the austenitic phase. It is understood that this phase change is what enables the characteristic recoverable strains achievable in superelastic nitinol.

Nitinol was originally developed by the military, but has found its way into many commercial applications. Applications that utilize the shape memory effect of the alloy include pipe couplings, orthodontic wires, bone staples, etc. Products that exploit the superelasticity of nitinol include, for example, antennas and eye glass frames.

The medical device industry has also found many uses for nitinol. Nitinol has been used to fabricate guide wires, cardiac pacing leads, prosthetic implants such as stents, intraluminal filters, and tools deployed through a cannula, to name a few. Such devices are taught in, for example, U.S. Pat. Nos. 4,665,906; 5,067,957; 5,190,546; 5,597,378; 6,306,141; and 6,533,805 to Jervis; U.S. Pat. Nos. 5,486,183; 5,509,923; 5,632,746; 5,720,754; 5,749,879; 5,820,628; 5,904,690; 6,004,330; and 6,447,523 to Middleman et al. An embolic filter can be made using nitinol as shown in, for example, U.S. Pat. No. 6,179,859 to Bates et al. Also, implantable stents have been made from nitinol as shown in, for example, U.S. Pat. No. 6,059,810 to Brown; U.S. Pat. No. 6,086,610 to Duerig. A guide wire can be made from nitinol, such as that shown in U.S. Pat. No. 5,341,818 to Abrams. Nitinol is also suitable for the construction of a cardiac harness for treating congestive heart failure as seen in, for example, U.S. Pat. No. 6,595,912 to Lau.

It is understood that all nitinol alloys exhibit both superelasticity and the shape memory effect. To maximize the benefits of each, the industry has developed processing techniques to control these characteristics. Those processing techniques include changing the composition of nickel and titanium, alloying the nickel-titanium with other elements, heat treating the alloy, and mechanical processing of the alloy. For instance, U.S. Pat. No. 4,310,354 to Fountain discloses processes for producing a shape memory nitinol alloy having a desired transition temperature. U.S. Pat. No. 6,106,642 to DiCarlo discloses a process for improving ductility of nitinol. U.S. Pat. No. 5,843,244 to Pelton discloses cold working and annealing a nitinol alloy to lower the $A_f$ temperature. United States Publication No. US 2003/0120181A1, published Jun. 26, 2003, is directed to work-hardened pseudoelastic guide wires. U.S. Pat. No. 4,881,981 to Thoma et al. is directed to a process for adjusting the physical and mechanical properties of a shape memory alloy member by increasing the internal stress level of the alloy by cold work and heat treatment.

One characteristic of nitinol that has not been greatly addressed is the cyclic fatigue life. In many devices, especially in medical applications, that undergo cyclic forces, fatigue life is an important consideration. There have been papers delivered on this topic such as W. Harrison, Z. Lin, "The Study of Nitinol Bending Fatigue," pp. 391-396; M. Reinoehi, et al., "The Influence of Melt Practice on Final Fatigue Properties of Superelastic NiTi Wires," pp. 397-403; C. Kugler, et at., "Non-Zero Mean Fatigue Test Protocol for NiTi," pp. 409-417; D. Tolomeo, et at., "Cyclic Properties of Superelastic Nitinol: Design Implications," pp. 461-471, all published by SMST-2000 Conference Proceedings, The International Organization Of Shape Memory And Superelastic Technology (2001). There is, however, still a need for developing a nitinol alloy that has improved fatigue life especially suitable for medical device applications.

INVENTION SUMMARY

The present invention is generally directed to a high fatigue life metal wire, ribbon, sheet, or tubing, and processes to create such forms. In one embodiment, the high fatigue life metal wire, ribbon, sheet, or tubing comprises a core made from a binary, nickel-titanium, superelastic alloy in an ingot state having a composition of approximately 54.5 to 57.0 weight percent nickel with a balance of titanium and trace elements. The nickel-titanium alloy preferably has an ingot $A_f$ temperature of approximately −15° C.±25° C.; and wherein the metal wire, ribbon, sheet, or tubing has undergone at least one cold work and anneal cycle with a final cold work of less than approximately 30% after a full anneal.

In a preferred embodiment, the metal wire, ribbon, sheet, or tubing has an ultimate tensile strength (UTS) of greater than or equal to approximately 150 ksi with an elongation at failure of greater than or equal to approximately 15%. The ultimate tensile strength and elongation specified are as measured at a temperature of approximately 23° C.±2° C. at a strain rate of approximately 0.001/sec.

The trace elements in the nickel-titanium alloy in the ingot state preferably include approximately less than or equal to 0.300 wt. % (3000 ppm) iron, less than or equal to 0.050 wt. % (500 ppm) copper, less than or equal to 0.050 wt. % (500 ppm) oxygen, less than or equal to 0.035 wt. % (350 ppm) carbon, and less than or equal to 0.003 wt. % (30 ppm) hydrogen. Furthermore, it is preferable that any other single trace element is less than 0.1 wt. % of the alloy. Total trace elements should be less than approximately 0.4 wt. %.

Further, the cold-drawn nitinol wire, ribbon, sheet or tubing is preferably heat treated between 450-500° C. and preferably has a final $A_f$ temperature between 26° C. and 36° C. as measured by Differential Scanning Calorimetry (DSC).

In various alternative embodiments, the metal wire has a diameter of approximately 0.0050 inch to 0.0160 inch. The wire may have a round or polygonal cross-sectional shape as with a ribbon. In accordance with the present invention, the high fatigue metal wire in a heat treated condition has a fatigue life greater than approximately 22,760 mean cycles to failure at a cyclic strain level of −0.75% to +0.75% at 37° C. as measured using a rotational beam test.

The present invention high fatigue life nitinol is preferably processed from an ingot of the composition specified above. The ingot is cold reduced or cold worked and annealed repeatedly to preferably a wire, ribbon, sheet, or tubing form. The nitinol is then cold worked through wire drawing, tube drawing, rolling, or like processes with interspersed anneal cycles for stress relief. As mentioned earlier, the final, after full anneal, cold working step is preferably limited to less than approximately 30% reduction in cross-sectional area to achieve the desired long fatigue life. In contrast, conventional processing of nitinol typically involves cold work at 35% or more.

The present invention in one embodiment limits the amount of the final cold work which, as confirmed through empirical observations, extends the fatigue life of the metal wire. The wire surface can be optionally electropolished to further improve the fatigue life. In a wire size around 0.013 inch in diameter, for example, the wire fatigue life in a heat treated condition has greater than approximately 22,760 mean cycles to failure under a rotational beam test where the tested wire is subjected to an alternating strain of ±0.75% at 37° C. By comparison, standard nitinol wires in the same size and the same heat treatment condition failed under the same test at about 16,560 cycles. Based on this data, the present invention wire represents about a 37% improvement in fatigue resistance. The present invention nitinol therefore has a dramatically improved fatigue life which is highly sought after in many applications where cyclic stress or strain is present.

From empirical observations, it was determined that the Ultimate tensile strength (UTS) and elongation to failure influenced the wire's fatigue resistance. Further, the amount of cold work applied to the wire during the drawing process also has an effect on the fatigue resistance. By controlling these parameters, the present invention produces a wire, ribbon, sheet or tubing having significantly improved fatigue life particularly suitable for medical device applications.

DETAILED DESCRIPTION OF THE PREFERRED EMBODIMENTS

Figure 1:
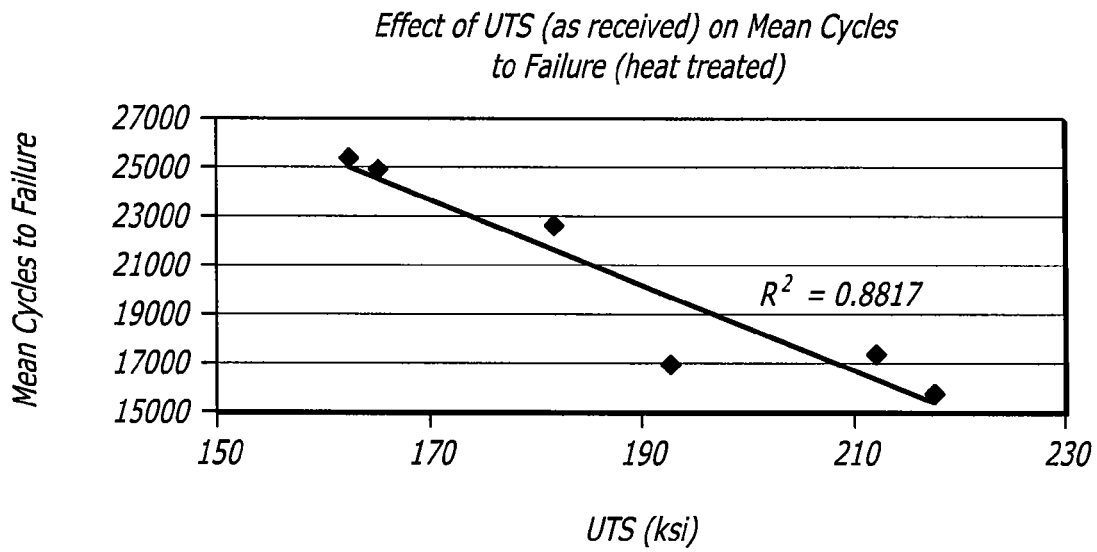
FIG. 1 is a graph of the effect on mean cycles to failure as a function of the ultimate tensile strength of a cold-drawn wire.

The present invention in various embodiments is directed to a wire, ribbon, sheet, tubing, or like structure made of superelastic nickel-titanium alloys having improved fatigue life and processes for creating such structures. Nickel-titanium alloys, also known as nitinol, have a variety of characteristics and behaviors based on processing conditions and composition. Products made from nitinol alloys nevertheless typically undergo a common series of processing steps.

For example, to produce commonly found structures such as wire, ribbon, tubing, or sheet, nickel and titanium charges are melted together to form an alloy ingot in a vacuum or inert atmosphere. Specifically, the constituent components are placed in a crucible, then induction heated or electrical arc heated in a vacuum induction melting (VIM) process or vacuum arc remelting (VAR) process, respectively. The nitinol ingot after VIM or VAR processing has the general composition of nickel to titanium as well as trace elements of carbon, oxygen, iron, and other impurities. After the melting process, the nitinol ingot has little ductility, and accordingly, it is preferable to hot work the ingot to achieve a microstructure that exhibits better workability.

To move the material closer to the desired mechanical and physical properties, the nitinol ingot undergoes a series of cold working steps. Typically, the nitinol receives cold working in the range of 40 to 50% at each step, and is also annealed at about 600 to 800° C. for stress release after each cold work step. The interspersed anneal cycles minimize work hardening of the nitinol caused by the repeated cold work. The cold working is typically performed by cold drawing for wires and ribbons through a series of dies; cold rolling for sheet stock; and tube drawing with an internal mandrel for tubes. To obtain the desired superelastic or shape memory properties, the nitinol alloy is usually heat treated after the last cold work step at about 450 to 550° C. Further details regarding conventional nitinol processing and fabrication are disclosed in, for example, Scott M. Russell, "Nitinol Melting and Fabrication," SMST-2000 Conference Proceedings, pp. 1-9 (2001), whose entire contents are hereby incorporated by reference. At this stage, the nitinol wire or ribbon, sheet stock, or tube has been transformed from raw materials into a standardized, nearly finished condition for consumption in the industry.

As explained earlier, the transformation temperature of the nitinol separates the austenitic phase from the martensitic phase. Typically, the transition temperature is measured by the austenite finish ($A_f$) temperature, which indicates the completion of the phase transformation from martensite to austenite during heating. The alloy transformation temperatures are determined by, among other factors, the ratio of nickel and titanium in the alloy. To be sure, the transformation temperatures are extremely sensitive to very small changes in the Ni—Ti composition. As a result, the presence of impurities or trace elements aside from nickel and titanium might unexpectedly change the transformation temperature of the alloy.

The $A_f$ temperature is commonly used as a metric in defining the characteristic of a nitinol device since it defines when the nitinol is completely in the austenitic phase. The $A_f$ temperature is usually measured by a technique called Differential Scanning Calorimetry (DSC) or by a "bend and free recovery" technique. The DSC technique detects the heat released and absorbed during the martensitic (exothermic) and austenitic (endothermic) transformations, respectively, and thus produces data indicating $A_f$ temperature. The bend and free recovery technique requires cooling the nitinol sample to a low temperature so that it is in the martensitic phase, bending the sample to a prescribed strain (typically 2% to 3%), and observing the temperature at which the sample returns to its original shape in the austenitic phase when heated, thus indicating the $A_f$ temperature.

Another metric for working with nitinol is the "ingot transition temperature." This is commonly defined as the $A_f$ temperature after a "full anneal" of the alloy. A full anneal implies that the alloy has been completely stress relieved, typically at about 750° C. for 5 to 10 minutes. The ingot transition temperature is usually measured by use of a DSC. The ingot transition temperature is indicative of the chemical composition of the alloy in the ingot state.

As is known in the art, heat treatment and cold work can change the transition temperature of the alloy. For a metric that reflects the processing received by the alloy, the "final $A_f$ temperature" is used. The final $A_f$ temperature is determined by using the DSC test on the alloy after it has been shape set to its remembered shape.

The present invention in various embodiments is directed to a high fatigue life metal wire, ribbon, tubing or sheet stock. In one preferred embodiment, the composition of the nitinol alloy in the ingot state includes about 55.8 weight percent nickel and about 44.2 weight percent titanium. In various alternative embodiments, the nickel composition may range from about 54.5 to 57.0 wt. % and everything therebetween, with the balance titanium (i.e., 45.5 to 43.0 wt. % and everything therebewteen). Trace elements or impurities may be present but are preferably limited to the following approximations: iron≦0.300 (3000 ppm); copper≦0.050 (500 ppm); oxygen≦0.050 (500 ppm); copper≦0.035 (350 ppm); and hydrogen≦0.003 (30 ppm). Any other single trace element should preferably be <0.1 weight percent. The total amount of trace elements present should be <0.4 weight percent. Furthermore, the ingot transformation temperature ($A_f$) as measured in the fully-annealed condition by the DSC technique should preferably be about −15° C.±25° C.

Once the composition and transformation temperatures for the ingot are set as above, the ingot undergoes a sequence of cold working and anneal cycles to reduce the ingot into preferably a wire, ribbon, tubing, or sheet of a desired cross-sectional area through the processing steps explained above.

In a preferred embodiment of the present invention, the "final" cold work or cold drawing step of the wire, ribbon, tubing or sheet stock is limited to less than approximately 30%, more preferably in the range of about 27%±3%. The "final" cold work or cold drawing step refers to the step immediately after a full anneal of the nitinol part in which the nitinol part undergoes a cold reduction or deformation changing the nitinol part into the desired final dimensions.

A further preferred embodiment of the present invention contemplates that the finished wire, ribbon, tubing, or sheet stock possess an ultimate tensile strength of approximately ≧150 ksi with an elongation at failure of approximately ≧15% as measured at a temperature of about 23° C.±2° C. at an approximate strain rate of 0.001 per second. More preferably, the UTS may be ≦190 ksi and ≧150 ksi including everything therebetween, while the elongation at failure may be ≦40% and ≧15% including everything therebetween. These parameters are again achieved through the sequence of cold work and anneal cycles mentioned above.

Once the foregoing conditions are met, one embodiment of the present invention nitinol wire with a 0.013 inch diameter exhibited a 37% increase in fatigue resistance over a conventional nitinol wire in a rotary beam fatigue test. In this test, the heat treated wire specimen with an $A_f$ temperature of 32±3° C. is gripped at the opposite ends where one end is motor driven and where both gripped ends are parallel and co-planar. The entire specimen is held within a vertical plane with the motor-driven end rotating to create alternating compressive and tensile strain in the specimen. The alternating strain ranged from about −0.75% to +0.75%. The specimen was also immersed in a water bath at 37° C. to approximate human body temperature. Being above the $A_f$ temperature of the wire, the ambient temperature also places the superelastic nitinol specimen in the austenitic phase. The motor-driven end rotated the specimen at a rate of 3,600 cycles per minute. In this test, the standard nitinol wire with a cold work of 40%±5% failed at an average of about 16,560 cycles; one embodiment of the present invention nitinol wire failed at about 22,760 cycles, which is an improvement of 37% in fatigue life.

In the above testing, a standard nitinol wire was used for comparison against one embodiment of the present invention. Both specimens were 0.013 inch diameter wire, with the same shape-setting heat treatment, having a nominal composition of 55.8 wt. % nickel and 44.2 wt. % titanium. Both have a total trace element composition of <0.4 wt. %. The following are the differences between the standard nitinol wire versus the present invention nitinol wire. Standard nitinol wire: 40%±5% final cold work; ingot $A_f$ temperature −15 to +15° C.; UTS≧190 ksi, elongation at failure≧6% at room temperature. Tested embodiment of invention: 27%±3% final cold work; ingot $A_f$ temperature −40 to +10° C.; UTS≧150 ksi, elongation at failure≧15% at room temperature.

The greatest difference between the standard wire versus the present invention wire is the amount of final cold work, where the amount of the final cold work step in the present invention wire is much lower. The expression "final cold work" as defined earlier is intended to mean the last cold work step bringing the part into its final dimensions, after a full anneal, and before the shape setting step where the shape memory is imparted into the alloy. From the test data, it is preferred that the final amount of area reduction by the cold working—such as wire drawing—is limited to less than 30%, and more preferably in the range of 27%±3% in order to help achieve the desired long fatigue life.

A coupon fatigue test was also used. The coupon test involves gripping the opposite ends of the specimen, which has a two-dimensional configuration imparted by the shape-setting treatment. The motorized test fixture then uniaxially tensions and releases the tension on the specimen. This is performed in a saline bath maintained at 37° C. The cycle rate of the test fixture is 15 cycles per second. At an aggressive loading condition of 80% to 120% stretch ratio based on the initial gauge length of the test specimen and corresponding to strain levels of approximately 0.9% to 1.4%. Under this test, the standard nitinol failed after an average of 7.3 hours (approximately 32000 cycles). Specimens of the present invention survived over 12 months (approximately 38 million cycles) and up to 15.3 months (approximately 48 million cycles) without failure. These empirical observations further confirmed the improved fatigue life of the present invention alloy and processing steps.

Figure 2:
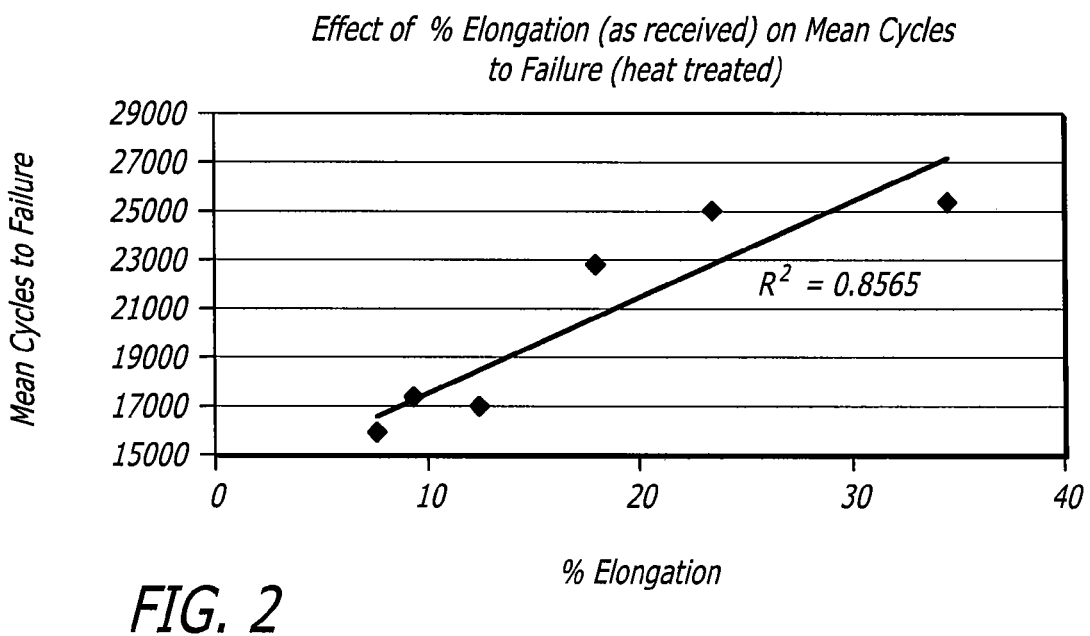
FIG. 2 is a graph of the mean cycles to failure as a function of percent elongation of a cold-drawn wire.

FIGS. 1 and 2 are plots of test data generated by 0.013 inch diameter nitinol wire made in accordance with the present invention. A rotational beam fatigue test was applied to these specimens using a 0% mean strain and an alternating strain of ±0.75%. FIG. 1 shows the influence of the ultimate tensile strength (UTS) on the mean cycles to failure. FIG. 2 is a plot showing the influence of percent elongation on the mean cycles to failure in the wire specimens. Note that the fatigue test was conducted after the shape-setting heat treatment on the specimens, but the UTS and elongation to fatigue were measured on the wire specimen in the as-drawn condition.

Figure 3:
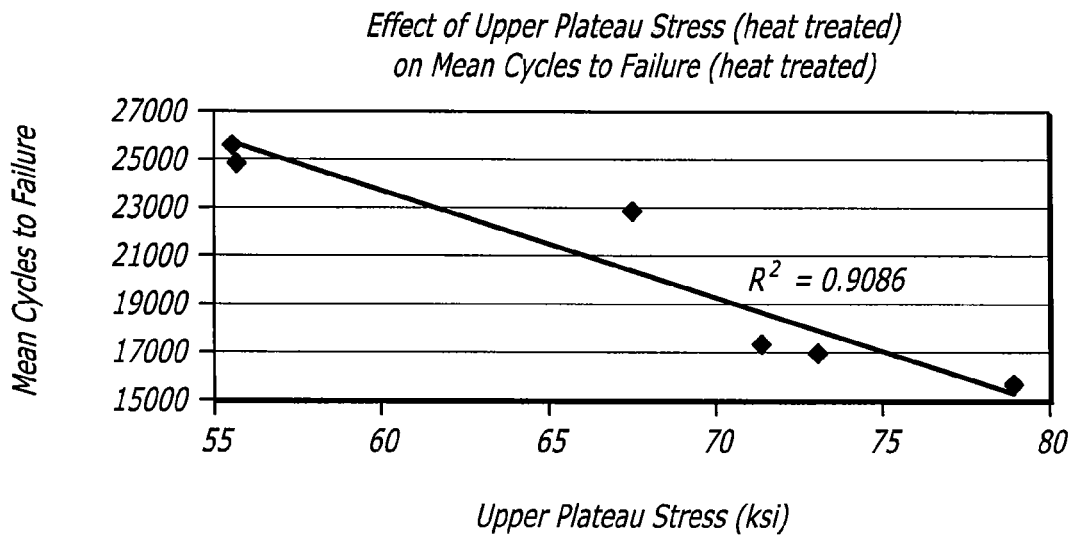
FIG. 3 is a graph of the effect on mean cycles to failure based on the upper plateau stress of a heat treated wire.
Figure 4:
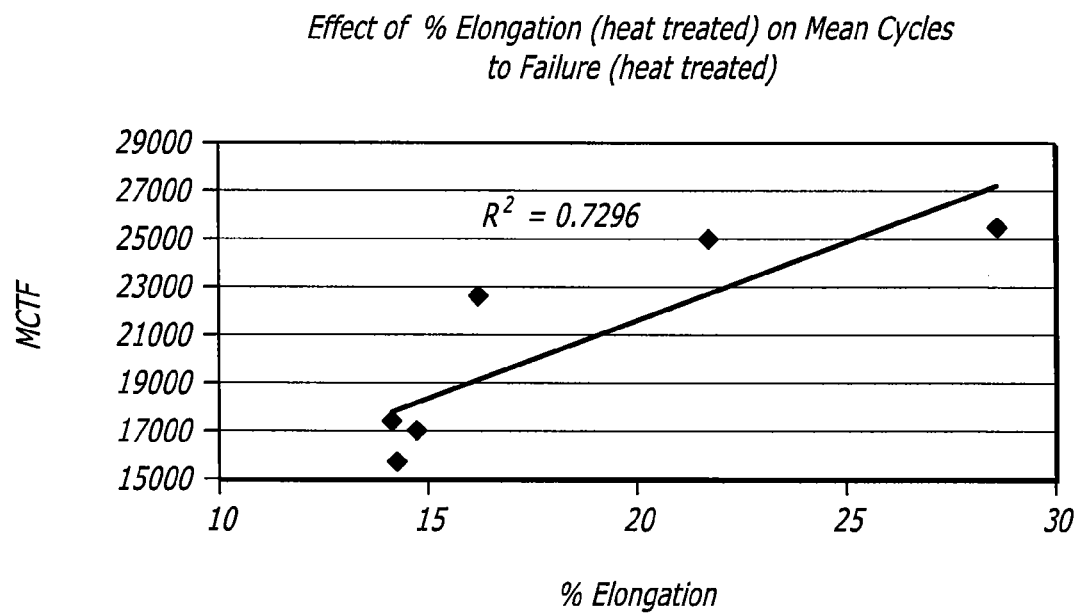
FIG. 4 is a graph of the effect on mean cycles to failure based on percent elongation of a heat treated wire.
Figure 5:
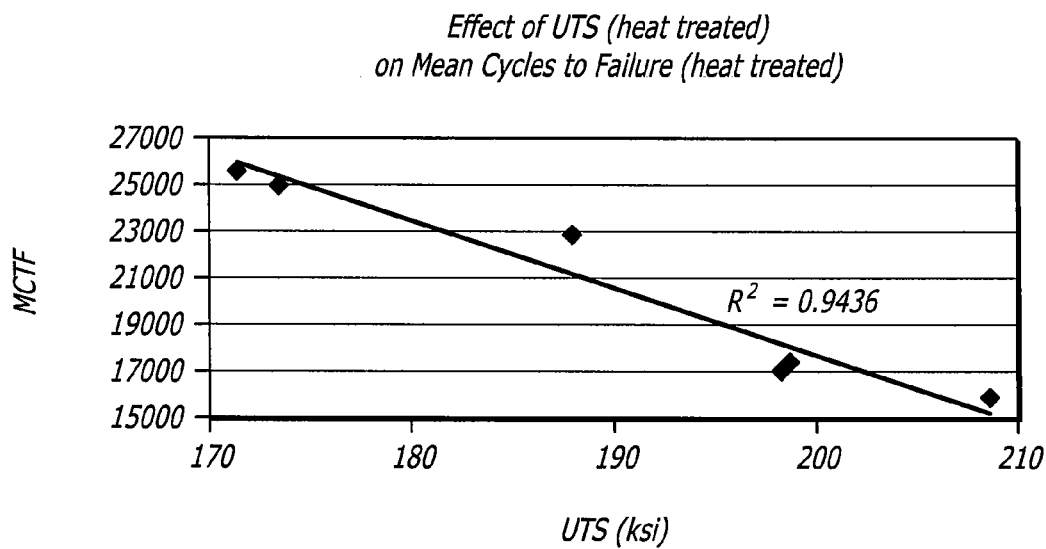
FIG. 5 is a graph of the effect on mean cycles to failure based on ultimate tensile strength of a heat treated wire.

FIGS. 3-5 are plots of the specimens described above under the same rotary beam fatigue test, but all properties were measured after the shape-setting heat treatment on the specimens. In FIG. 3, the upper plateau stress (from the superelastic nitinol stress-strain "flag" curve) of the superelastic nitinol alloy is plotted against the mean cycles to failure. In FIG. 4, the percent elongation is plotted against the mean cycles to failure while in FIG. 5, the ultimate tensile strength is plotted against the mean cycles to failure.

Based on the foregoing plots and other empirical observations, it was determined that in order to achieve an improved fatigue life, it is desirable to limit the final cold work step after the precursor cycles of cold drawing and annealing, to less than approximately 30%, and more preferably in the range of 27%±3%, and even down to 24%. Ideally, the ultimate tensile strength should preferably be set at ≧150 ksi with an elongation at failure preferably set at ≧15%.

The tested specimens in the described rotary beam fatigue test were not polished after the shape setting heat treatment. Therefore, they exhibited a blue oxide surface.

The present invention nitinol wire, ribbon, tubing or sheet stock can be shape set to the desired shape through processes known in the art. This is usually accomplished by manipulating the nitinol wire, ribbon, tubing, or sheet into a fixture duplicating the remembered shape. The nitinol wire, ribbon, tubing or sheet is heated to well above the alloy's martensite deformation temperature ($M_d$). For a wire, ribbon, tubing, or sheet, the shape set temperature is typically in the range of 250-600° C.; the heating occurs for an average of a few minutes up to an hour, with longer times for lower temperatures and vice versa.

The cold-drawn nitinol wire embodiment is preferably heat treated between 450-500° C. and preferably has a final $A_f$ temperature between 26° C. and 36° C. as measured by the DSC technique.

The blue oxide surface formed from the shape setting heat treatment can optionally be removed by electropolishing. This further improves fatigue resistance. Moreover, the final $A_f$ temperature of the formed wire can optimally be adjusted by the shape setting heat treatment without deviation from the scope of the present invention.

Figure 6:
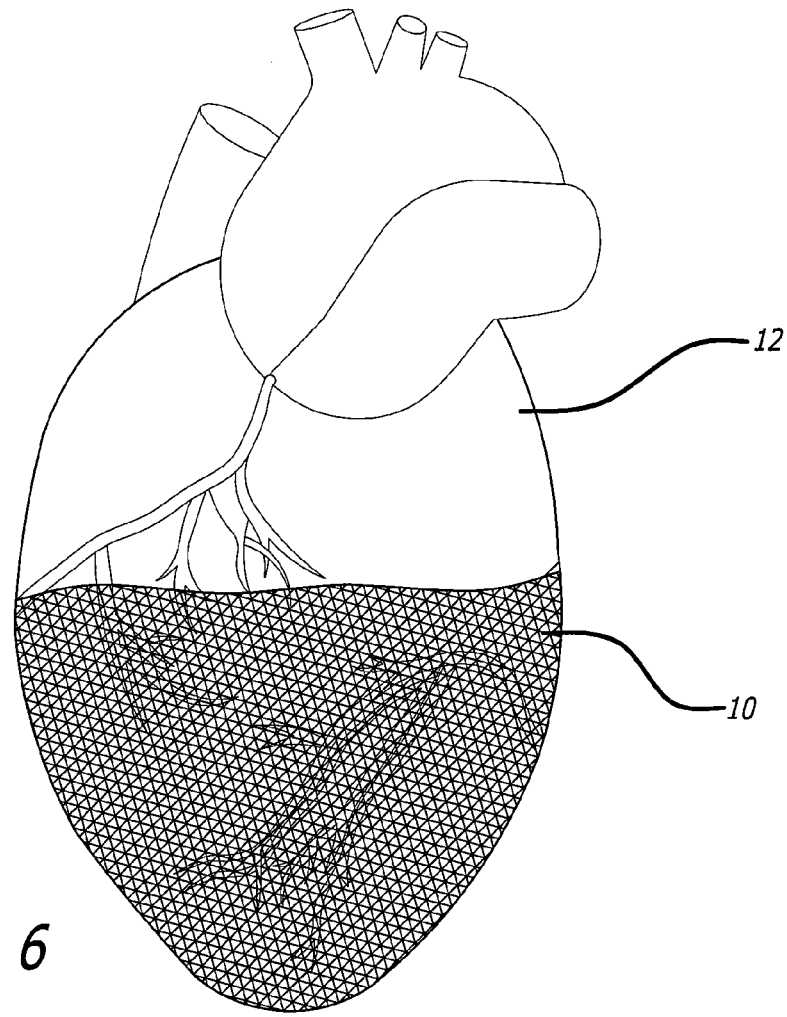
FIG. 6 is a perspective view of a cardiac harness made from a matrix of wires having high fatigue life in accordance with the present invention.

In one preferred application, the present invention high fatigue life wire or ribbon can be constructed into a matrix or wire mesh for use as a cardiac harness for treating congestive heart failure, shown in FIG. 6. The wires or ribbons may be interlocked, interwoven, or otherwise joined together forming a sleeve. If a sheet or tube of the present invention high fatigue life nitinol is chosen as the foundation, then it can be laser cut, electro-discharge machined, chemically etched, or likewise cut to create a pattern of openings to form a matrix that is then shaped into a sleeve also suitable for use as a cardiac harness.

In a patient with congestive heart failure, the diseased myocardium begins to remodel which typically manifests in the heart enlarging into a more spherical shape. One type of treatment is to implant an external elastic support or constraining sleeve for the myocardium. Such a constraining sleeve, called a cardiac harness 10, is seen in FIG. 6. In this embodiment, the cardiac harness 10 surrounds both ventricles, from apex to base of the heart 12. As the ventricle dilates in congestive heart failure, outward radial pressure is applied to the cardiac harness 10; conversely, the cardiac harness applies a constraining pressure on the heart.

More important is the systole and diastole contraction and relaxation of the heart which apply repeated cyclical pressure on the cardiac harness 10. Due to this cyclic stress, the cardiac harness should exhibit a relatively high fatigue life after implantation in the patient. Therefore, the wires forming the cardiac harness 10 are made from superelastic nitinol in accordance with the present invention embodiments and are in the austenitic phase at body temperature when no load is applied and the alloy is stress-free. When placed over the heart as shown in FIG. 6, the contact pressure between the harness 10 and heart 12 may create stress-induced martensite (SIM) in the material. Depending on the stress-strain "flag" curve of the superelastic nitinol alloy, the actual stress encountered by the nitinol wire may fall on a stress plateau or may be sufficiently low to fall in the linear stress-strain range. In any event, the present invention high fatigue life wire minimizes the possibility under such conditions of a fracture or fatigue failure in the harness. More details regarding the cardiac harness 10 may be found in, for example, U.S. Pat. No. 6,595,912 to Lau et al., whose entire contents are hereby incorporated by reference.

Another medical application of the high fatigue life wire is in the area of implantable stents. A stent implanted in a vessel behind the knee would certainly encounter cyclic stresses and strains and long fatigue life becomes an important consideration. Other applications include, for example, eyeglass frames, cell-phone or radio antennas. Such applications expose the wire to cyclic stresses and strains, and a high fatigue life is unquestionably a valuable engineering asset.

Various modifications may be made to the present invention without departing from the scope thereof. Although individual features of embodiments of the invention may be shown in some of the drawings and not in others, those skilled in the art will recognize that individual features of one embodiment of the invention can be combined with any or all of the features of another embodiment.

We claim:

1. A high fatigue life wire, ribbon, sheet or tubing, comprising:
    a core including a binary, nickel-titanium, superelastic alloy in an ingot state having a composition of approximately 54.5 to 57.0 wt. % nickel with a balance of titanium, and trace elements;
    the nickel-titanium alloy having an ingot $A_f$ at approximately −15° C.±25° C.;
    wherein the core has undergone at least one cold work and full anneal cycle with a final cold work of less than approximately 30%; and
    wherein the core has a fatigue life>approximately 20,000 mean cycles to failure under compressive and tensile strain of −0.75% to +0.75%.

2. The high fatigue life wire, ribbon, sheet or tubing of claim 1, wherein the core has an ultimate tensile strength of≧approximately 150 ksi in the cold worked condition.

3. The high fatigue life wire, ribbon, sheet or tubing of claim 1, wherein the core has an elongation at failure of≧approximately 15% in the cold worked condition.

4. The high fatigue life wire, ribbon, sheet or tubing of claim 1, wherein the core includes a round cross-section.

5. The high fatigue life wire, ribbon, sheet or tubing of claim 1, wherein the core includes a polygonal cross-section.

6. The high fatigue life wire, ribbon, sheet or tubing of claim 1, wherein the core includes a surface that is at least partially polished.

7. The high fatigue life wire, ribbon, sheet or tubing of claim 1, wherein the trace elements in the nickel-titanium alloy includes approximately:
    ≦0.300 wt. % (3000 ppm) Fe,
    ≦0.050 wt. % (500 ppm) Cu, ≦0.050 wt. % (500 ppm) O,
≦0.035 wt. % (350 ppm) C, and
≦0.003 wt. % (30ppm) H.

8. The high fatigue life wire, ribbon, sheet or tubing of claim 1, wherein any other single trace element is <0.1 wt. %.

9. The high fatigue life wire, ribbon, sheet or tubing of claim 1, wherein the core includes an ultimate tensile strength≧approximately 150 ksi, and elongation at failure≧approximately 15%, as measured at a temperature of approximately 23±2 ° C. and at a strain rate of approximately 0.001/sec.

10. A wire, ribbon, sheet or tubing made from a high fatigue life shape memory material, comprising:
- a core including a binary, nickel-titanium, superelastic alloy in an ingot state having a composition of approximately 54.5 to 57.0 wt. % nickel with a balance of titanium, and trace elements of<approximately 0.4 wt. %;
- the nickel-titanium alloy having an ingot $A_f$ at approximately −15° C. ±25° C.;
- wherein the core includes an ultimate tensile strength≧approximately 150 ksi, and elongation at failure≧approximately 15%, as measured at a temperature of approximately 23±2° C. and a strain rate of approximately 0.001/sec.; and
- wherein the core has a fatigue life>approximately 20,000 mean cycles to failure under compressive and tensile strain of −0.75% to +0.75%.

11. The wire, ribbon, sheet or tubing of claim 10, wherein the core has been cold worked and annealed with a final cold work that is less than approximately 30%.

12. The wire, ribbon, sheet or tubing of claim 10, wherein the high fatigue life is measured while immersed in a liquid at a temperature above the Af of a heat treated condition.

13. The wire, ribbon, sheet or tubing of claim 10, wherein the core has a diameter of approximately 0.0050 to 0.0160 inch.

14. The wire, ribbon, sheet or tubing of claim 10, wherein the core has been cold worked through a final cold drawing to reduce a cross-sectional area thereof by less than 30%.

15. A medical device for implantation, comprising:
- a sleeve having elastic compliance under expansion forces;
- wherein the sleeve includes a binary, nickel-titanium, superelastic alloy in an ingot state having a composition of approximately 54.5 to 57.0 wt. % nickel with a balance of titanium, and trace elements;
- wherein the nickel-titanium alloy includes an ingot $A_f$ at approximately −15° C.±25° C.; and
- wherein the nickel-titanium alloy includes an ultimate tensile strength of≧approximately 150 ksi, and elongation at failure is≧approximately 15%, as measured at a temperature of approximately 23±2° C., at a strain rate of approximately 0.001/sec.; and
- wherein the sleeve has a fatigue life>approximately 20,000 mean cycles to failure under compressive and tensile strain of −0.75% to +0.75%.

16. The medical device of claim 15, wherein the sleeve includes a plurality of wires with a final cold work of less than approximately 30%.

* * * * *